United States Patent [19]

Battista et al.

[11] Patent Number: 4,661,638

[45] Date of Patent: Apr. 28, 1987

[54] CATALYST DERIVED FROM MIXTURE OF MANGANESE HYDROXIDE AND MAGNESIUM-CONTAINING MATERIAL, AND METHOD OF USE IN ORTHO-ALKYLATION OF PHENOLS

[75] Inventors: Richard A. Battista, Mt. Vernon, Ind.; James G. Bennett, Jr., Glenmont; John J. Kokoszka, Delmar, both of N.Y.; Freddie L. Tungate, Georgetown, Ind.

[73] Assignee: General Electric Company, Selkirk, N.Y.

[21] Appl. No.: 776,192

[22] Filed: Sep. 16, 1985

Related U.S. Application Data

[62] Division of Ser. No. 612,795, May 22, 1984, abandoned.

[51] Int. Cl.$^4$ ............................................. C07C 37/00
[52] U.S. Cl. ..................................... 568/804; 568/794
[58] Field of Search ................................ 568/804, 794

[56] References Cited

U.S. PATENT DOCUMENTS

| | | | |
|---|---|---|---|
| 3,843,606 | 10/1974 | Van Sorge | 568/804 |
| 3,873,628 | 3/1975 | Van Sorge | 568/804 |
| 3,971,832 | 7/1976 | Watanabe et al. | 568/804 |
| 3,972,836 | 8/1976 | Van Sorge | 568/804 |
| 3,974,229 | 8/1976 | Van Sorge | 568/804 |
| 4,418,224 | 11/1983 | Bennett et al. | 568/804 |
| 4,503,272 | 3/1985 | Bennett et al. | 568/804 |
| 4,528,407 | 7/1985 | Smith et al. | 568/804 |
| 4,547,480 | 10/1985 | Bennett et al. | 568/804 |
| 4,551,563 | 11/1985 | Talley | 568/804 |

FOREIGN PATENT DOCUMENTS 2127083  12/1971  Fed. Rep. of Germany ...... 568/805

*Primary Examiner*—Werren B. Lone
*Attorney, Agent, or Firm*—Michael J. Doyle

[57] ABSTRACT

A catalyst precursor prepared by precipitating manganese hydroxide from caustic solution and then mixing the precipitate with a magnesium-containing material is described. The catalyst precursor can be calcined to an active form, and the resulting catalyst can be used to effect or facilitate the ortho-alkylation of phenolic compounds in vapor phase reactions. Superiority of performance is demonstrated with respect to a catalyst derived from a precursor in which manganese hydroxide is precipitated (sometimes referred to as "co-precipitation") in the presence of a magnesium compound, rather than formed separately.

18 Claims, 1 Drawing Figure

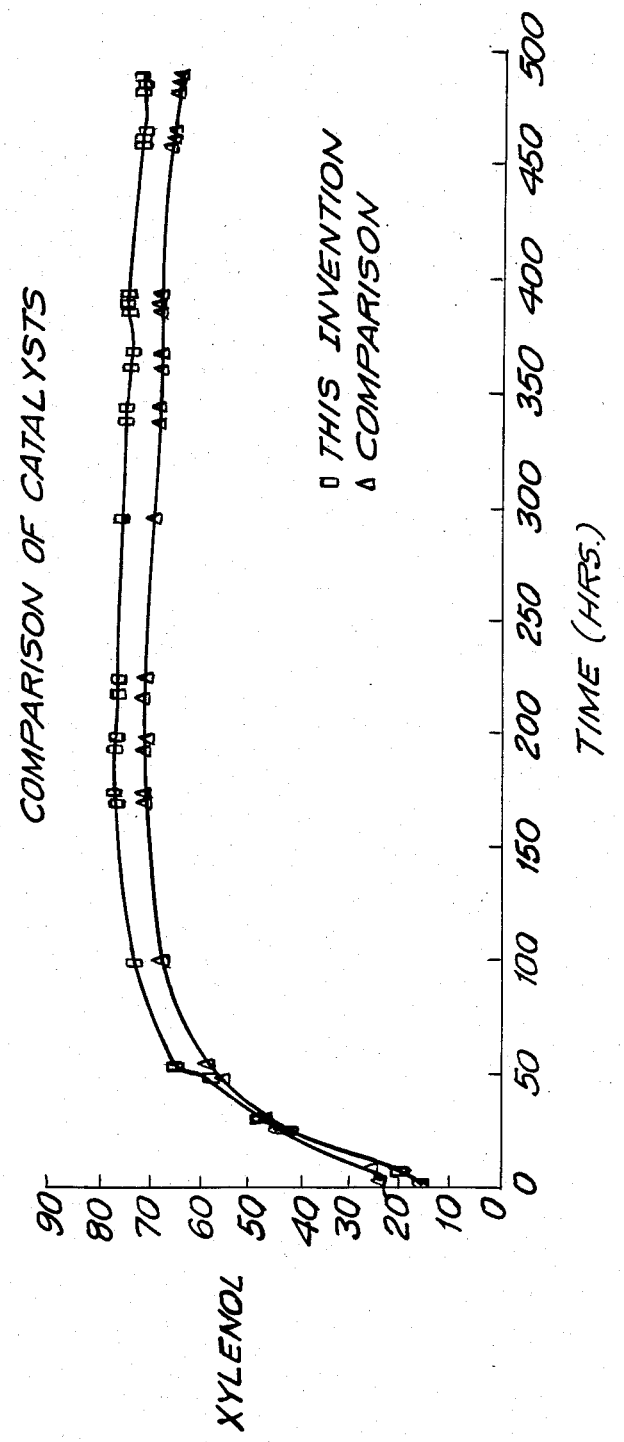

CATALYST DERIVED FROM MIXTURE OF MANGANESE HYDROXIDE AND MAGNESIUM-CONTAINING MATERIAL, AND METHOD OF USE IN ORTHO-ALKYLATION OF PHENOLS

This a division of application Ser. No. 612,795 filed May 22, 1984 now abandoned.

BACKGROUND OF THE INVENTION

Phenolic compounds containing alkyl substituents in the ortho position on the ring are useful as starting materials for the preparation of polyphenylene oxide resins. In general, these compounds are prepared by catalyzed processes in which one or more phenolic compounds are reacted with an alkyl alcohol in the vapor phase. A number of specific procedures are described in the patent literature.

Processes designed for the ortho-methylation of phenols are disclosed by Hamilton, in U.S. Pat. Nos. 3,446,856 and 3,479,410. The first employs magnesium oxide as a catalyst at a temperature from 475° to 600° C. The second uses magnesium oxide or calcium phosphate, under similar conditions. In both cases, the magnesium oxide can be derived by thermal decomposition of magnesium carbonate, which can occur using the same temperatures as employed in the ortho-alkylation reaction. In addition, Van Sorge, in U.S. Pat. No. 3,972,828, describes an ortho-alkylation catalyst consisting of powdered magnesium oxide together with an inert polymeric binder.

Catalysts based on both magnesium and manganese have been found useful in ortho-alkylation reactions. Some of these are formed by co-precipitation, others by dry blending. In co-precipitation, manganous hydroxide is precipitated from a solution of a manganese salt in the presence of a magnesium source, e.g., magnesium carbonate. Precipitation can be induced by heating, by the addition of a caustic, e.g., potassium or sodium hydroxide, or addition of ammonium hydroxide. These kinds of procedures are described in copending U.S. applications Ser. Nos. 163,452 and 163,486, both filed Jun. 27, 1980 and assigned to the same assignee as herein. Dry blending techniques, on the other hand, are based in general on the admixing of magnesium oxides with manganese oxides or of compounds of the two which are capable of conversion into oxides upon calcination. See, for example, U.S. Pat. No. 3,873,628(mixing magnesium oxide and manganese sulfate, heating to dryness, and calcining), and U.S. Pat. Nos. 3,972,836 and 3,974,229(blending powders of magnesium oxide and manganese oxide).

Many of the above mentioned types of magnesium manganese catalysts suffer from shortcomings of one kind or another. Those which employ caustic co-precipitation techniques usually result in a catalyst which must be thoroughly washed to remove residual amounts of sodium or potassium ions. The use of ammonia is often objectionable because of the strong odor. Procedures in which sulfates are the manganese source can result in giving off malodorous fumes.

INTRODUCTION TO THE INVENTION

The discovery has now been made that a catalyst precursor having the capability of being calcined to a highly active state can be prepared by admixing a magnesium containing material with manganese hydroxide, in which the manganese hydroxide has been preformed separately by precipitation from an aqueous mixture of a manganese salt solution and a caustic solution. The precursor can be calcined to a catalyst which is useful in a process for the ortho-alkylation of phenols. In comparison with a catalyst precursor made by the precipitation of manganese hydroxide from hot solution in the presence of the magnesium compound, the present kind of precursor after calcining exhibits better activity, as is shown in comparative test experiments described in this disclosure and in the accompanying drawing.

This invention thus comprises several aspects. One aspect is the catalyst precursor itself; that is, the catalyst prior to being activated. Another aspect is the catalyst precursor having been formed by a certain specific combination of process steps, to be described below. A third aspect is a process for the formation of the active catalyst, including a calcining treatment. A fourth aspect is the catalyst formed by this process, which is shown to be different from another catalyst formed from the same starting materials, but using different process steps. Finally, another aspect comprises an improved method for the ortho-alkylation of phenolic compounds, using the described catalyst.

DESCRIPTION OF THE DRAWING

FIG. 1 is a graph which compares the performance of a catalyst in accordance with the invention with that of a catalyst according to the prior art in an ortho-alkylation process for the production of 2,6- xylenol. Further details are given in the description of the examples.

DESCRIPTION OF THE INVENTION

The catalyst precursor is formed as a mixture of a magnesium-containing material and manganese hydroxide. The manganese hydroxide is derived by bringing together an aqueous solution of a soluble manganese compound and an aqueous caustic solution. Suitable manganese compounds, which may be used individually or in admixture as the source of manganese, include relatively soluble compounds such as manganese nitrate, manganese sulfate and manganese acetate. Also contemplated, however, are other water soluble materials, such as manganese chloride, manganese bromide, and the like.

By way of illustration, a solution of the manganese compound or compounds in water is formed and to it is gradually added a solution of a caustic in water. The caustic may be an alkali metal salt, such as sodium hydroxide or potassium hydroxide. The addition is accompanied with stirring and will normally take place over a period from about 10 to 30 minutes, during which a precipitate of manganese hydroxide forms. The procedure may be, and preferably is, conducted at or near room temperature, e.g., about 25° C. Recovery of the manganese hydroxide may be accomplished by filtration or centrifugation, after which it is preferably washed, dried to remove most of the moisture, and then ground or pulverized into a fine powder, for example, from 25 to 50 mesh, U.S. Standard Sieve.

The manganese hydroxide formed in this manner is then blended with a magnesium material. Suitable magnesium materials include magnesium carbonate, basic magnesium carbonate and magnesium hydroxide, individually or in admixtures of two or more. The term "basic magnesium carbonate" refers to those materials represented by the formula $$xMgCO_3 \cdot Mg(OH)_2 \cdot xH_2O$$

in which each x independently is a number average from about 3 to 5.

Preferably, the magnesium material is basic magnesium carbonate, and especially in finely divided form.

The manganese compound and magnesium material can be employed in varying proportions to form the catalyst precursor, but preferably they are used in amounts so as to provide from about 0.02 to about 0.25 moles of manganese for each mole of magnesium in the final catalyst composition.

The catalyst precursor, comprising a mixture of finely divided particles of magnesium material and manganese hydroxide, is then preferably blended with a binder material or materials to facilitate shaping and subsequent processing. As a binder material there may be used various inorganic or organic substances, both polymeric and non-polymeric. The preferred binder is a polymer, and especially preferred are polyphenylene ether resins such as those which are described by Allan Hay in U.S. Pat. Nos. 3,306,874 and 3,306,875. Polyphenylene ether copolymers may also be used. The polyphenylene ether resin, for instance, may be compounded with the catalyst precursor particles in an amount from about 0.1 up to about 20% by weight. The polymer can be used alone or together with other materials, such as powdered graphite or a similar shaping aid in an amount of up to about 3.0 % by weight.

The mixture of catalyst precursor particles and binder is then shaped into the desired form, which may be accomplished using virtually any suitable shaping method or device. Illustratively, and preferably, the solid mixture is formed into tablets on a press, utilizing conventional conditions. Alternatively, the mixture of particles can also be shaped into cylinders, pellets, or any of the other forms conventional for catalyst preparation.

After being shaped, the catalyst precursor is activated for use by being subjected to a calcining treatment under time and temperature conditions sufficient to produce an active catalyst. Typically, the treatment involves heating the precursor to a temperature of at least 300° C., or sufficient to convert the magnesium and manganese compounds to a mixture of oxides. Temperatures of between approximately 350 and 500° C. for a period of about 34 hours are preferred, but temperatures as high as 550 ° C. may be used. Calcining can be effected in a variety of environments, including air, an inert gas, e.g., nitrogen, or under vacuum. The calcination treatment may be carried out prior to loading into a reactor, or alternatively, in situ in the reactor itself, and optionally in the presence of a feed stream of the reactants.

During the calcining step, it will be found that minute pores form in the catalyst, thereby exposing more surface area, which is beneficial to the ultimate performance. A surface area of at least 25, and preferably from 25 to 450, square meters per gram of catalyst weight is very desirable and will normally be achieved using the conditions which have been described.

The catalyst prepared in the aforementioned manner may be employed to effect or facilitate the ortho-alkylation of phenolic compounds, such as those having the formula

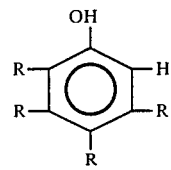

in which each R, independently, is a monovalent substituent selected from the group consisting of hydrogen, alkyl (preferably $C_1$ to $C_{12}$ alkyl), phenyl, and alkyl substituted phenyl (preferably $C_1$ to $C_{12}$ alkyl substituted phenyl).

The alkyl alcohol which is the co-reactant in the process is preferably a branched or linear saturated alcohol having up to 16 carbon atoms, such as methyl, ethyl, propyl, isopropyl, butyl, isobutyl, tert.-butyl, amyl, isoamyl, hexyl, heptyl, octyl, nonyl, decyl, lauryl, cetyl, cyclohexyl, and the like. Especially preferred are alcohols having up to 6 carbon atoms, with methanol being the most preferred.

By way of illustrating the practice of the process, any one or a mixture of phenols having an ortho hydrogen is vaporized and, together with an alkyl alcohol, is passed through a reactor heated to a temperature of at least 300° C., preferably from about 400 ° to 500° C., and containing a catalyst prepared as described. For the most favorable results, it is advisable to use at least one mole of the alkyl alcohol, and preferably from one to three moles, for each ortho position on the phenol to be alkylated. For example, if phenol, which has two ortho hydrogens per molecule, is to be methylated to produce 2, 6-xylenol in optimum yields, it is desirable to employ from two to six moles of methanol for each mole of phenol, the larger yields being obtained with use of the higher ratios of methanol to phenol.

The ortho-alkylation process can be carried out under a variety of reaction conditions of temperature, pressure, flow rate of reactants, vapor space velocity of reactants over catalyst, contact time of reactants with catalyst, length of catalyst feed, and so forth. Above a temperature of 500° C., however, decomposition of the reactants and products often becomes a problem, and such temperatures should be avoided.

Generally, the reaction conditions are regulated to minimize the amount of unreacted feed materials which must be recovered and reused, and to maximize the percentage of selectivity to the desired ortho-alkylated end products, that is, phenolic compounds having an alkyl substituent in the "2" or both the "2" and "5" positions (relative to the hydroxy group) on the ring.

While the reaction proceeds at atmospheric pressure, which is preferred, superatmospheric pressures or subatmospheric pressures can be used if desired.

The vapors issuing from the reactor are condensed, and the products are separated by conventional methods, such as crystallization or distillation.

Using the present catalyst, yields of the desired ortho-alkylated end product are good, with selectivity being favored over meta and para alkylations.

DESCRIPTION OF THE SPECIFIC EMBODIMENTS

The invention in its various aspects is illustrated in the following examples, which are not to be construed as limiting.

EXAMPLE 1

A catalyst precursor in accordance with the invention was prepared as follows:

An amount consisting of 16.1 grams of a 50% aqueous solution of sodium hydroxide was dissolved in 250 milliliters of distilled water, then placed in an addition funnel. Separately, 35.8 grams of a 50% by weight solution of manganous nitrate was dissolved in 500 milliliters of distilled water. The sodium hydroxide solution was added gradually to the manganese nitrate solution, with stirring, at a rate of 5 to 10 milliliters per minute, during which a precipitate comprising manganese hydroxide formed. The mixture was filtered to separate the mother liquor from the precipitate, using a 600-milliliter-capacity medium fritted filter. After the filtration was completed, 250 milliliters of distilled water were poured into the filter cake, which was still wet, and using a handheld homogenizer the cake was resuspended in the water, after which it was vacuum filtered. The procedure was repeated four more times to thoroughly clean the precipitate. The wet filter cake was left in the fritted funnel and placed in a vacuum oven at a temperature of 108° C. overnight to dry. The dried cake was removed from the oven the following morning, ground through a No. 25 sieve, and blended with magnesium carbonate on a jar mill using a weight ratio of 2.5:97.5 of manganese hydroxide:magnesium carbonate. The blend was, in turn, mixed with poly(2,6-dimethyl-1,4-phenylene ether)resin (PPO ®, General Electric Company), also on the jar mill, using amounts to provide a 90:10 ratio of catalyst precursor:PPO. The resulting mixture of solids was formed into 3/16 inch by 150 inch tablets on a tabletting press.

For purposes of comparison, a catalyst precursor in accordance with the prior art was prepared as follows:

518.9 grams of basic magnesium carbonate having four waters of hydration (the formula above in which x =4) was slurried in 2000 milliliters of distilled water. Forty grams of a 50% by weight aqueous manganous nitrate solution was diluted with 450 milliliters of water, and then added gradually to the slurry over a 5-minute period, with stirring. The resulting mixture was blanketed with a stream of nitrogen gas and maintained at a temperature of 80° C., for 3 hours, with stirring continued. A precipitate of manganese hydroxide was formed. The precipitate was centrifuged to separate it from the mother liquor, and then oven dried. The resulting dried powder was blended with poly(2,6-dimethyl-1,4-phenylene ether)resin (PPO) of less than 140 mesh particle size, using a 90:10 by weight ratio of catalyst precursor to PPO ®. Powdered graphite was added (Asbury Chemical's 99) in an amount of 0.5% by weight, and the graphite-containing mixture was compacted using a roller mill, screened, and formed into 3/16 inch by 150 inch tablets.

EXAMPLE 2

The catalyst precursors of Example 1 were then calcined to activate them for use in a process for the ortho-methylation of a phenolic compound. In both cases, calcination was conducted in situ in an ortho-alkylation reactor, which is described as follows:

THE REACTOR

The Reactor comprises two stainless steel tubes, both disposed along a verticle axis, one of which has a length of 15 inches (38.1 centimeters), the other of which has a length of 24 inches (60.96 centimeters), and both of which have an inner diameter of ¾inch (1.91 centimeters). The first functions as a vaporizer. The second is filled to a depth of two inches with glass beads that serve as a support for the catalyst and functions as a reactor. Both are partially immersed in a fused salt bath, the first to a depth of 8 inches (20.3 cm), the second to a depth of 17 inches (43.2 cm). The first (vaporizer) and second (reactor) tubes are joined by a third tube, consisting of a two inch long (5.1 cm) steel pipe connected at one end to an opening in the first tube 5 inches (12.7 cm) from its bottom, and at the other end to an opening in the second tube 14 inches (35.6 cm) from its bottom. The connector tube also passes through the fused salt bath.

In practice, a feed stream comprising the reactants is sent from a reservoir, through a metering pump, into the first (vaporizer) tube, where the feed stream is heated to a temperature high enough to volatilize the constituents. The vapors emitting from the vaporizer tube pass through the interconnecting pipe, which serves as a preheater to bring the vapors up to the temperature of the reactor tube. The vapors are fed from there to the reactor tube and the catalyst bed, where reaction takes place. Product vapors leave the bottom of the reactor tube through a stainless steel outlet tube, having an inner diameter of ⅜ inch (0.95 cm), and are led to a water-cooled condenser and receiver where they are liquefied and recovered. The non-condensible materials are fed to an off-gas meter, where they can be measured.

In each case, the reactor was charged with 110 ml. of the catalyst precursor, capped, and placed in the fused salt bath at a temperature of 370 ° C., after which a stream of gaseous nitrogen was blown over the catalyst bed at a rate of 2 standard cubic feet per hour (SCFH). After 15 minutes, a feed stream of the reactants was started. The feed comprised a mixture of methanol, phenol and orthocresol, in a 4:1 ratio by weight of methanol to phenolics. The weight ratio of phenol to orthocresol was 60:40. The feed also contained about 20% water. The feed rate was held at 215 ml/hour, which was equivalent to a liquid hourly space velocity (LHSV) of 1.95. The pressure for this experiment was maintained at one atmosphere.

After the temperature of the feed was established at 370 ° C., it was raised to 458° C. where it was maintained throughout the run. The product stream was sampled periodically to analyze for the constituents. The percentages of unreacted phenol and orthocresol, of 2,6-xylenol (the desired end product), and of 2,4,6-trimethyl phenol (a byproduct) were calculated, and from these data the selectivity to the dessired end product was also computed. The test results are reported in Table 1 below.

TABLE 1

| Catalyst | Time, hrs. | Off Gas, SCFH | Wt. % Phenol | Wt. % O—Cresol | Wt. % 2,6 | Wt. % 2,4,6 | Selectivity |
|---|---|---|---|---|---|---|---|
| This Invention | 506 | 0.684 | 3.03 | 21.05 | 71.08 | 4.20 | 16.9 |

TABLE 1-continued

| Catalyst | Time, hrs. | Off Gas, SCFH | Wt. % Phenol | Wt. % O—Cresol | Wt. % 2,6 | Wt. % 2,4,6 | Selectivity |
|---|---|---|---|---|---|---|---|
| Comparison | 506 | 0.537 | 3.99 | 24.89 | 65.66 | 4.80 | 13.7 |

The results are plotted in the accompanying FIGURE. As can be seen, the process conducted in accordance with the invention produces a distinctly higher yield of 2,6-xylenol (the top line in the graph), over virtually the entire duration of the run.

EXAMPLE 3

The procedure of Example 2 was repeated, with the exception that the reaction was conducted using a pressure equivalent to 25 atmospheres and a temperature of about 435 to 440° C. The comparative results are listed in Table 2 below.

TABLE 2

| Catalyst | Time, hrs. | Off Gas SCFH | Wt. % Phenol | Wt. % O—Cresol | Wt. % 2,6 | Wt. % 2,4,6 | Selectivity |
|---|---|---|---|---|---|---|---|
| This Invention | 342 | 0.735 | 1.78 | 11.85 | 75.44 | 9.61 | 7.9 |
| Comparison | 190* | 0.237 | 3.99 | 21.92 | 60.66 | 11.16 | 5.4 |

*Run stopped at 190 hours due to plugged reactor

All of the above mentioned patents are incorporated herein by reference.

Other variations and modifications of the invention are possible, and changes may be made in the specific embodiments shown which are within the scope of the invention defined in the appended claims.

We claim:

1. In a process for the alkylation of a phenolic compound in the ortho position by the vapor phase reaction, in the presence of an alkylation catalyst, of a feed mixture of an alkyl alcohol which is a branched or linear saturated alcohol having up to about 16 carbon atoms, and one or more phenolic compounds represented by the formula

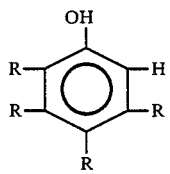

in which R is independently, a monovalent substituent selected from the group consisting of hydrogen, alkyl, phenyl, and alkyl-substituted phenyl groups, the improvement in which the catalyst product derived by heating a catalyst precursor comprising a solid mixture of a magnesium-containing material and manganese hydroxide, the manganese hydroxide having been formed separately as a precipitate by bringing together an aqueous solution of a soluble manganese compound and a aqueous solution of a caustic.

2. A process according to claim 1, in which the feed mixture comprises methanol, phenol and ortho-cresol, and the end product comprises 2,6-xylenol.

3. A process according to claim 1, in which the catalyst has been formed from a solid mixture of manganese hydroxide and a magnesium compound or compounds selected from a group consisting of magnesium carbonate, basic magnesium carbonate and magnesium hydroxide.

4. A process according to claim 3, in which the magnesium compound is magnesium carbonate.

5. A process according to claim 3, in which the magnesium compound is basic magnesium carbonate.

6. A process according to claim 3, in which the magnesium compound is magnesium hydroxide.

7. A process according to claim 3, in which the manganese hydroxide has been precipitated from an aqueous solution of manganese nitrate, manganese sulfate, or manganese acetate.

8. A process according to claim 1 in which the catalyst contains from about 0.02 to 0.25 moles of manganese per mole of magnesium.

9. A process according to claim 1, in which the catalyst includes a binder material.

10. A process according to claim 9 which the binder material is a polymer.

11. A process according to claim 10, in which the polymer is a polyphenylene ether resin.

12. A process according to claim 10, in which the binder material is poly(2,6-dimethyl-1-1 4-phenylene ether).

13. A process according to claim 10, in which the catalyst is porous and has a surface area from about 25 to 450 square meters per gram of catalyst weight.

14. A process according to claim 1, in which the ortho-alkylation reaction is conducted at a temperature of at least 300° C.

15. A process according to claim 14, in which the reaction temperature is in the range from about to 500° C.

16. A process according to claim 1, which is conducted under a pressure of about one atmosphe;re.

17. A process according to claim 1, in which the catalyst has been calcined in situ in the same ortho-alkylation reactor in which the process is conducted.

18. A process according to claim 1 in which the catalyst has been calcined prior to being loaded into the ortho-alkylation reactor in which the process is conducted.

* * * * *